US012688914B2

(12) United States Patent
Nichols et al.

(10) Patent No.: US 12,688,914 B2
(45) Date of Patent: Jul. 21, 2026

(54) METHODS AND SYSTEMS FOR IMPLEMENTING PERSONALIZED HEALTH APPLICATION

(71) Applicant: SandwYch, Inc., Austin, TX (US)

(72) Inventors: Deborah L. Nichols, Battle Ground, IN (US); Amy B. Blakely, Austin, TX (US)

(73) Assignee: SandwYch, Inc., Austin, TX (US)

( * ) Notice: Subject to any disclaimer, the term of this patent is extended or adjusted under 35 U.S.C. 154(b) by 120 days.

(21) Appl. No.: 18/399,449

(22) Filed: Dec. 28, 2023

(65) Prior Publication Data

US 2024/0221882 A1      Jul. 4, 2024

Related U.S. Application Data

(60) Provisional application No. 63/436,553, filed on Dec. 31, 2022.

(51) Int. Cl.
| | |
|---|---|
| *G16H 40/67* | (2018.01) |
| *G16H 10/60* | (2018.01) |
| *G16H 20/00* | (2018.01) |
| *G16H 50/20* | (2018.01) |
| *G16H 50/70* | (2018.01) |
| *G16H 80/00* | (2018.01) |

(52) U.S. Cl.
CPC ............. *G16H 20/00* (2018.01); *G16H 10/60* (2018.01); *G16H 40/67* (2018.01); *G16H 50/20* (2018.01); *G16H 50/70* (2018.01); *G16H 80/00* (2018.01)

(58) Field of Classification Search
CPC ........ G16H 20/00; G16H 10/60; G16H 40/67; G16H 50/20; G16H 50/70; G16H 80/00; G16H 10/20
See application file for complete search history.

(56) References Cited

U.S. PATENT DOCUMENTS

| | | | |
|---|---|---|---|
| 11,404,170 B2 | 8/2022 | Charlap | |
| 11,854,708 B2 * | 12/2023 | Streat ..................... | G16H 10/20 |
| 2017/0162069 A1 | 6/2017 | Petakov et al. | |
| 2017/0300648 A1 | 10/2017 | Charlap | |

(Continued)

OTHER PUBLICATIONS

Kankanhalli, A., Xia, Q., Ai, P., & Zhao, X. (2021). Understanding personalization for health behavior change applications: A review and future directions. AIS Transactions on Human-Computer Interaction, 13(3), 316-349.

(Continued)

*Primary Examiner* — Sheetal R Paulson
(74) *Attorney, Agent, or Firm* — Stovall Legal, PLLC; Blake D. Stovall

(57) ABSTRACT

A method for generating a graphical user interface (GUI) can include receiving a first user request to log in to a session of an application. The method can further include obtaining first user characteristic information, including one or more user psychological information, user environmental information, or user lifestyle information. The method can further include selecting a first set of GUI elements to be presented to the user during the session, wherein the first set of GUI elements are selected based on the first user characteristic information. The method can further include generating a GUI that includes the first set of GUI elements and transmitting the GUI to a user device for display during the session.

20 Claims, 15 Drawing Sheets

(56) References Cited

U.S. PATENT DOCUMENTS

2020/0411170 A1 * 12/2020 Brown ................... G06N 20/00
2022/0277841 A1 * 9/2022 Harmon ................ G16H 40/20

OTHER PUBLICATIONS

Mckee, K. J., Brown, J., & Nolan, M. (2006). Services for Supporting Family Carers of Older Dependent People in Europe: Characteristics, Coverage and Usage. The Trans-European Survey Report. EUROFAMCARE, European Commission, Deliverable 19.

Mele, C., Spena, T. R., Kaartemo, V., & Marzullo, M. L. (2021). Smart nudging: How cognitive technologies enable choice architectures for value co-creation. Journal of Business Research, 129, 949-960.

Mora, A., Riera, D., González, C., & Arnedo-Moreno, J. (2017). Gamification: a systematic review of design frameworks. Journal of Computing in Higher Education, 29, 516-548.

Soap Health, http://soap.health, as visited Apr. 25, 2024.

Zarzycki, M., & Morrison, V. (2021). Getting back or giving back: Understanding caregiver motivations and willingness to provide informal care. Health Psychology and Behavioral Medicine, 9(1), 636-661.

* cited by examiner

200

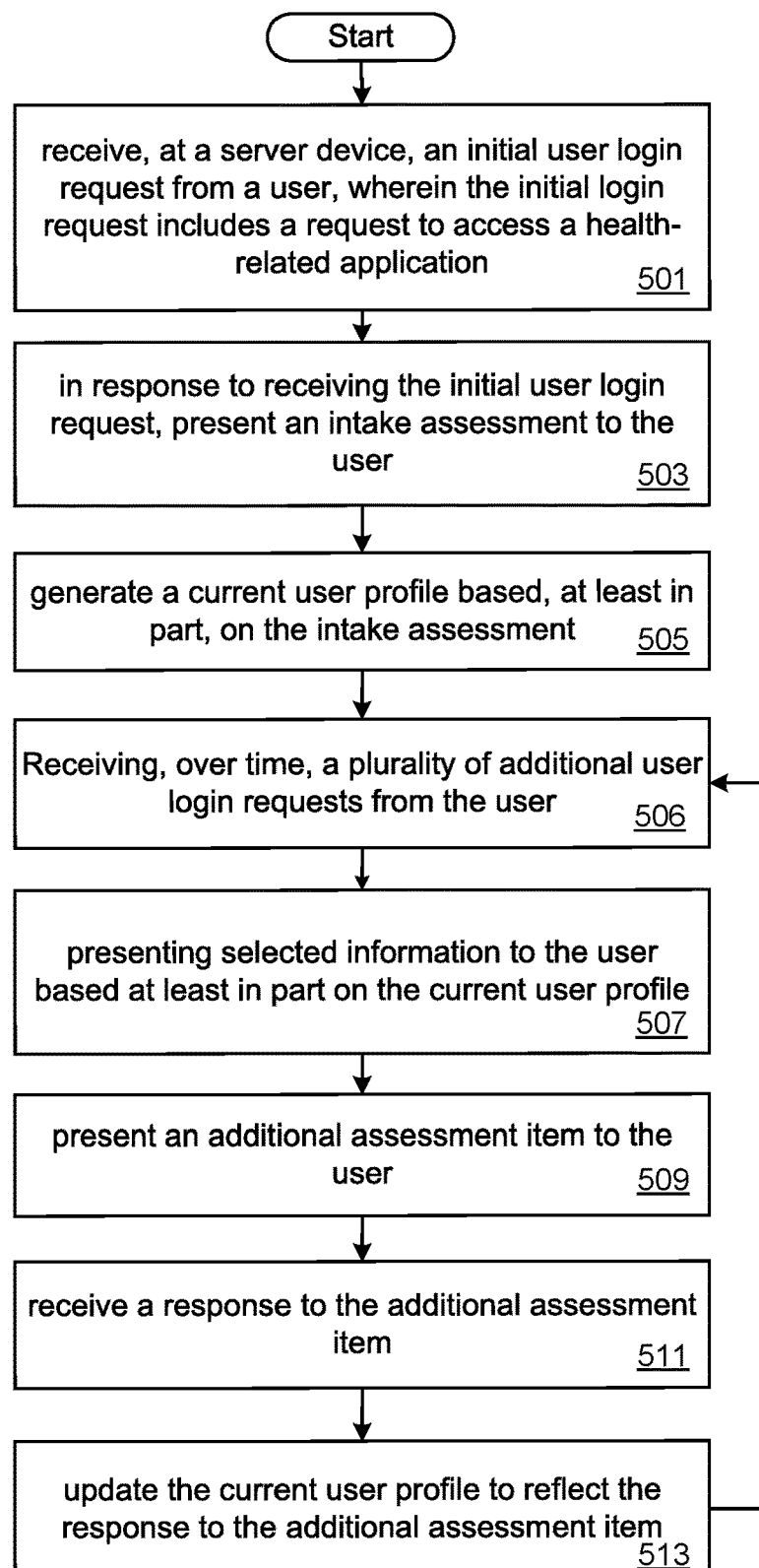

receive, at a server device, an initial user login request from a user, wherein the initial login request includes a request to access a health-related application     501 in response to receiving the initial user login request, present an intake assessment to the user     503 generate a current user profile based, at least in part, on the intake assessment     505

Receiving, over time, a plurality of additional user login requests from the user     506 presenting selected information to the user based at least in part on the current user profile     507 present an additional assessment item to the user     509 receive a response to the additional assessment item     511 update the current user profile to reflect the response to the additional assessment item     513

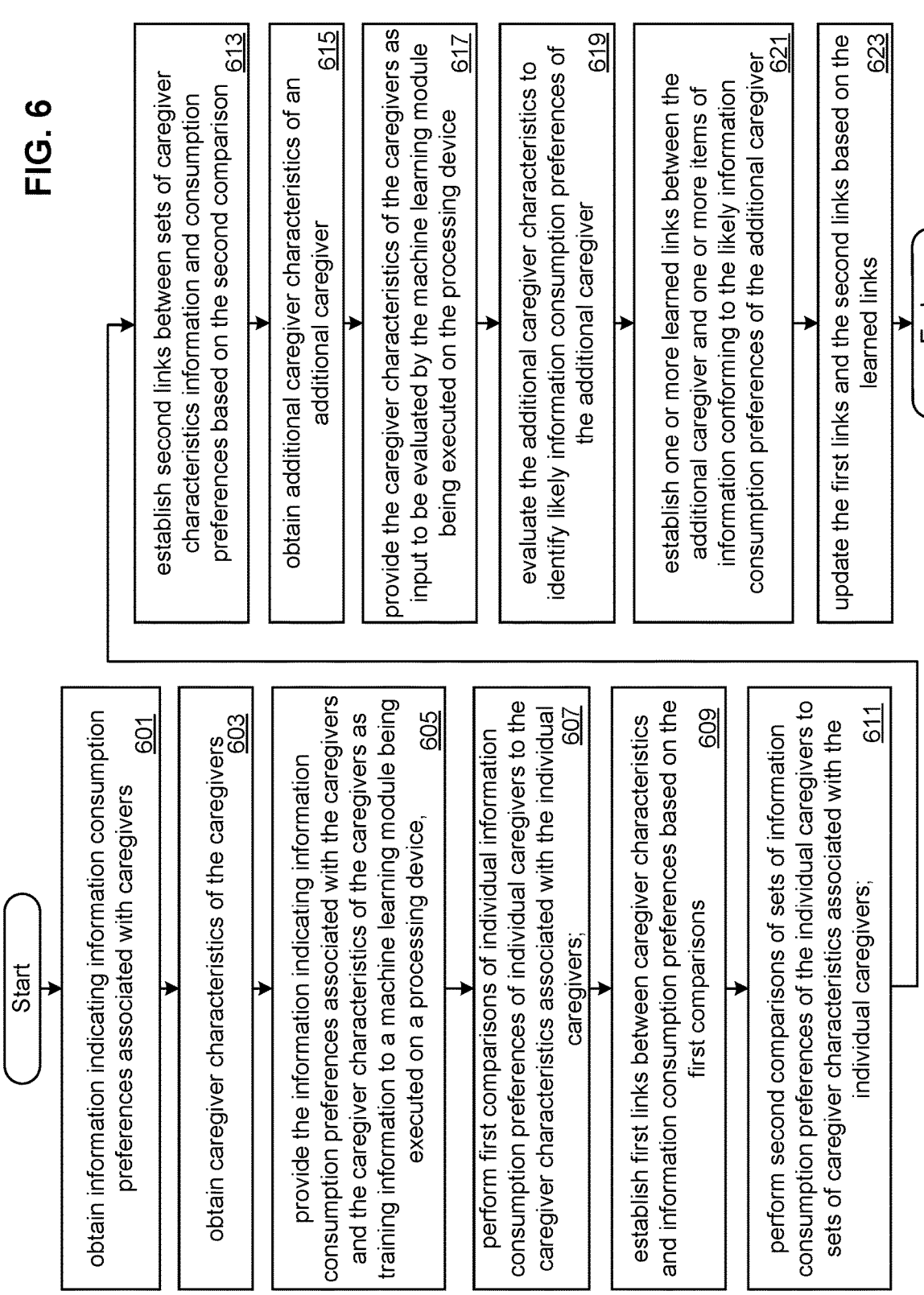

Start obtain information indicating information consumption preferences associated with caregivers 601 obtain caregiver characteristics of the caregivers 603 provide the information indicating information consumption preferences associated with the caregivers and the caregiver characteristics of the caregivers as training information to a machine learning module being executed on a processing device, 605 perform first comparisons of individual information consumption preferences of individual caregivers to the caregiver characteristics associated with the individual caregivers; 607 establish first links between caregiver characteristics and information consumption preferences based on the first comparisons 609 perform second comparisons of sets of information consumption preferences of the individual caregivers to sets of caregiver characteristics associated with the individual caregivers; 611 establish second links between sets of caregiver characteristics information and consumption preferences based on the second comparison 613 obtain additional caregiver characteristics of an additional caregiver 615 provide the caregiver characteristics of the caregivers as input to be evaluated by the machine learning module being executed on the processing device 617 evaluate the additional caregiver characteristics to identify likely information consumption preferences of the additional caregiver 619 establish one or more learned links between the additional caregiver and one or more items of information conforming to the likely information consumption preferences of the additional caregiver 621 update the first links and the second links based on the learned links 623

End

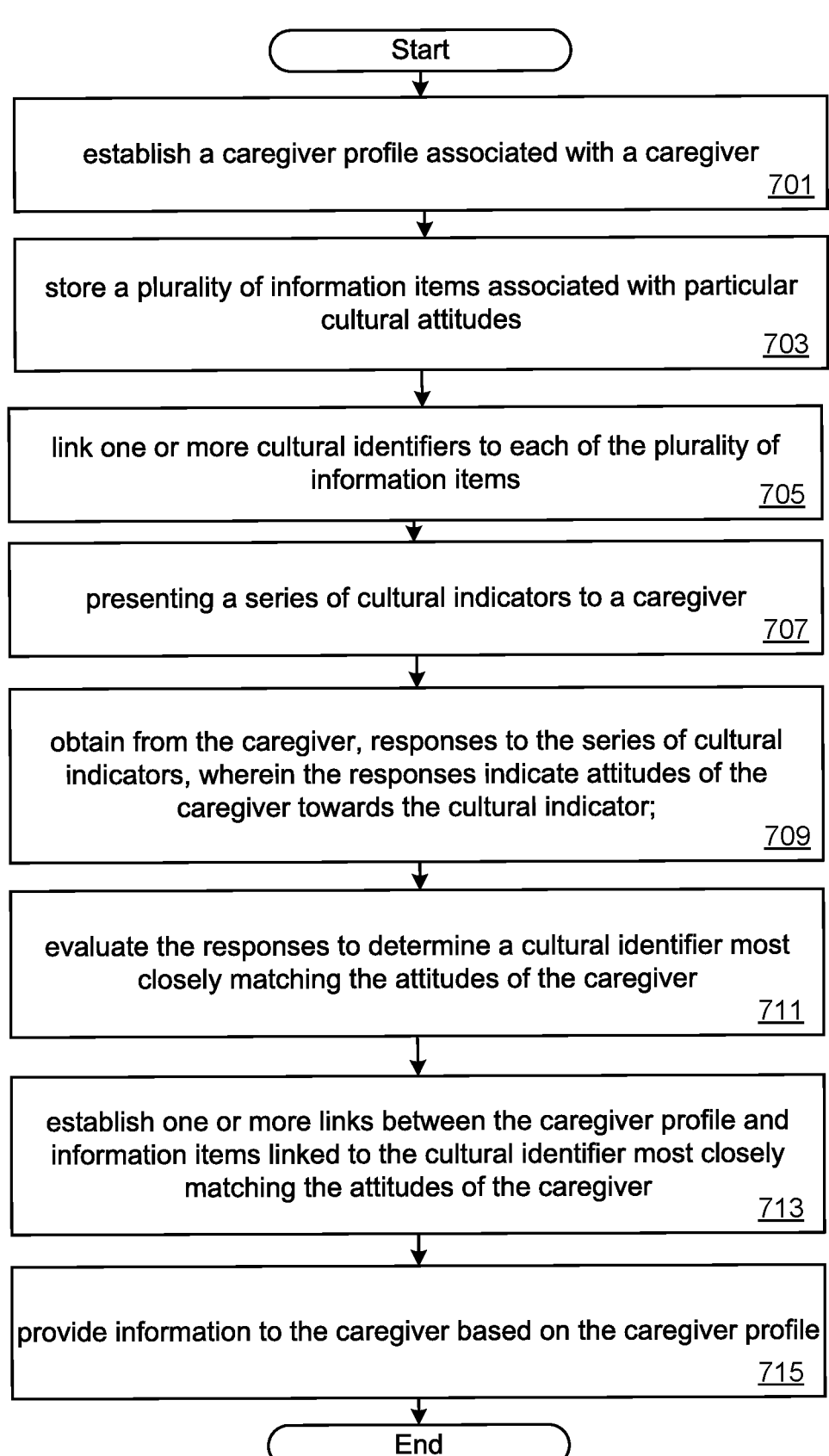

Start establish a caregiver profile associated with a caregiver
701 store a plurality of information items associated with particular cultural attitudes
703 link one or more cultural identifiers to each of the plurality of information items
705 presenting a series of cultural indicators to a caregiver
707 obtain from the caregiver, responses to the series of cultural indicators, wherein the responses indicate attitudes of the caregiver towards the cultural indicator;
709 evaluate the responses to determine a cultural identifier most closely matching the attitudes of the caregiver
711 establish one or more links between the caregiver profile and information items linked to the cultural identifier most closely matching the attitudes of the caregiver
713 provide information to the caregiver based on the caregiver profile
715

End

FIG. 7

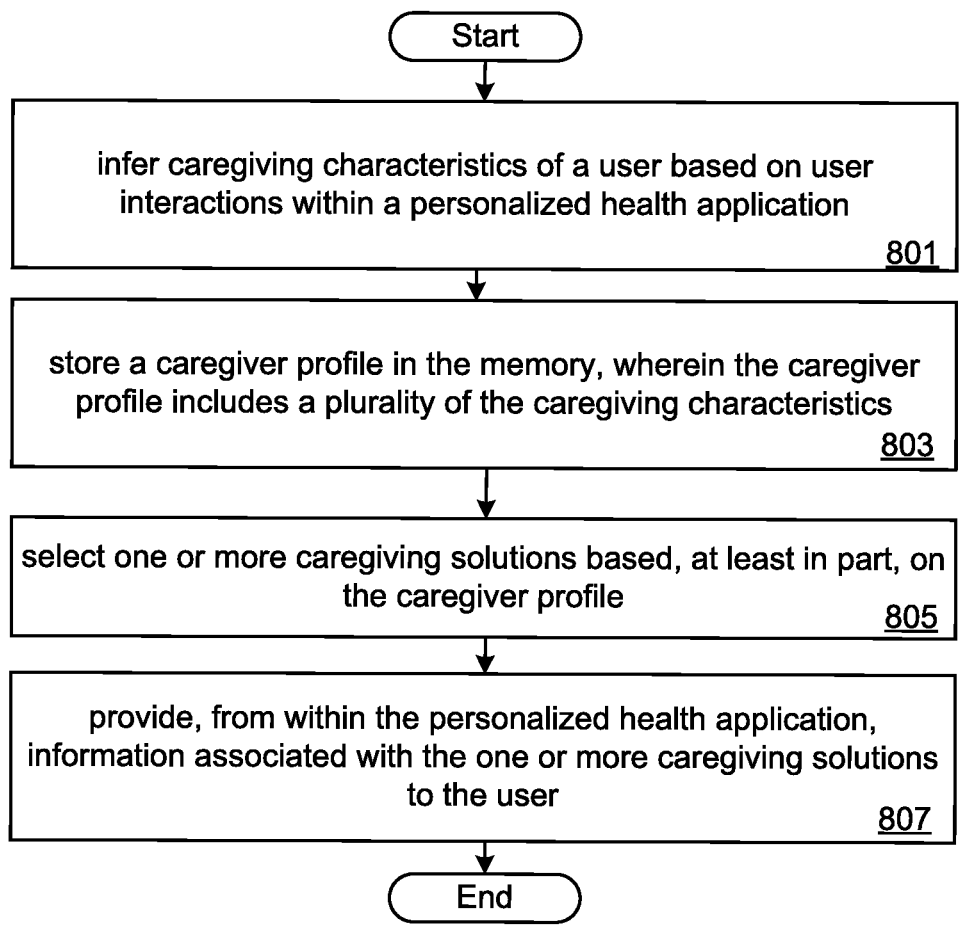

infer caregiving characteristics of a user based on user
interactions within a personalized health application
                                                              801 store a caregiver profile in the memory, wherein the caregiver
profile includes a plurality of the caregiving characteristics
                                                              803 select one or more caregiving solutions based, at least in part, on
the caregiver profile
                                                              805 provide, from within the personalized health application,
information associated with the one or more caregiving solutions
to the user
                                                              807

Pick one

903 → A.) I have a long road ahead of me.

905 → B.) I feel peaceful.

907 → C.) I'm looking forward to an adventure.

METHODS AND SYSTEMS FOR IMPLEMENTING PERSONALIZED HEALTH APPLICATION

BACKGROUND OF THE INVENTION

Technical Field of the Invention

This invention relates generally to methods and systems for implementing computer applications, and more specifically to methods and systems for implementing health applications providing information tailored for individual users.

Description of Related Art

Various weight loss and fitness applications are commercially available, but conventional applications do not provide personalized support for caregivers.

BRIEF DESCRIPTION OF THE SEVERAL VIEWS OF THE DRAWING(S)

FIG. 5 is a flow diagram illustrating a method of determining user preferences in accordance with embodiments of the present disclosure;

FIG. 6 is a flow diagram illustrating a method employing machine learning/artificial intelligence in accordance with embodiments of the present disclosure;

FIG. 7 is a flow diagram illustrating a method of using a caregiver profile in accordance with embodiments of the present disclosure;

FIG. 8 is a flow diagram illustrating a method for use in a system in accordance with embodiments of the present disclosure;

FIG. 9 is a diagram illustrating a one-question mood assessment in accordance with embodiments of the present disclosure;

DETAILED DESCRIPTION OF THE INVENTION

Figure 1:
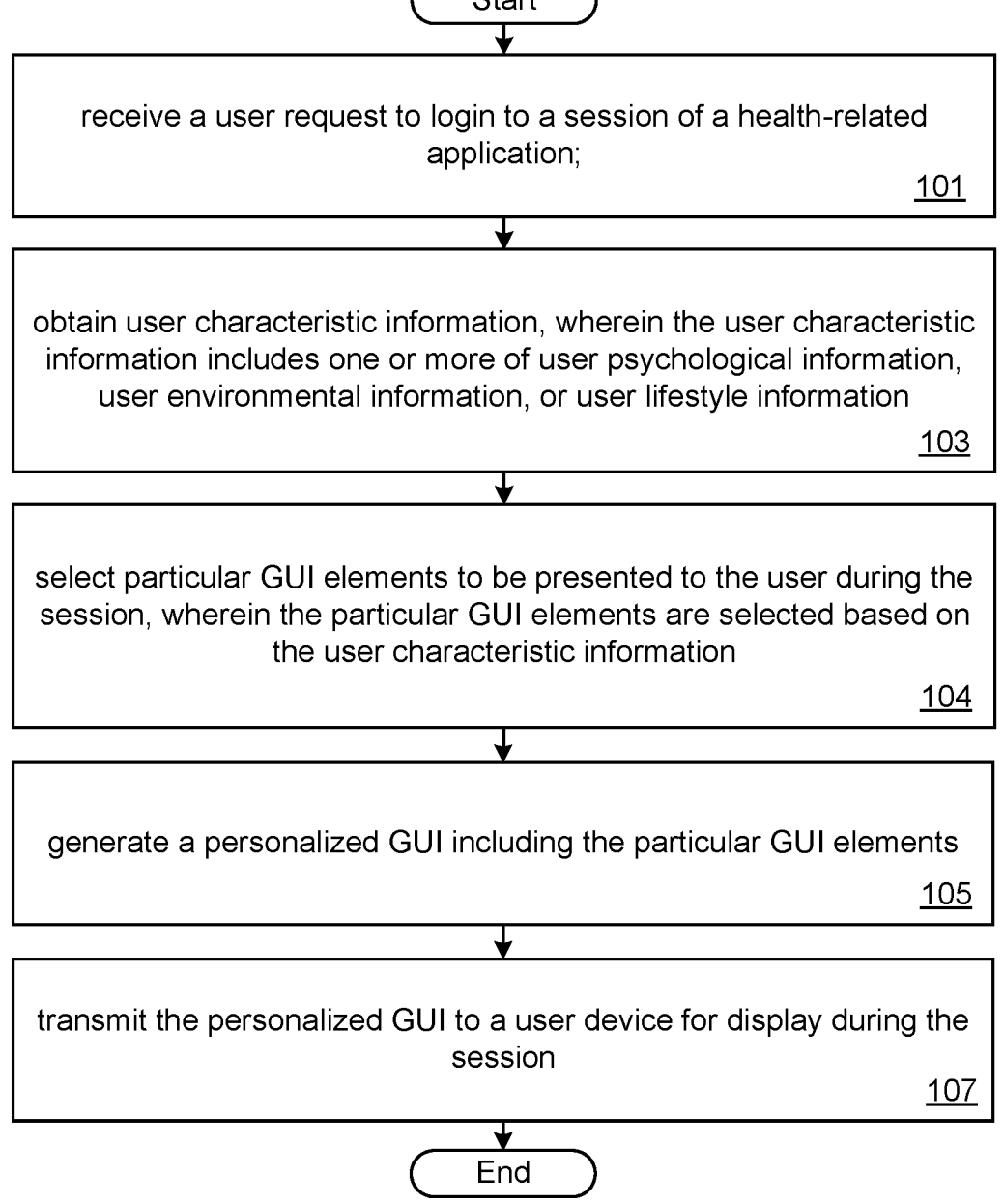
FIG. 1 is a flow diagram illustrating a method of generating a personalized graphical user interface (GUI) in accordance with embodiments of the present disclosure.

Described herein are various embodiments of a personalized health application, including a personalized medicine mobile health application designed to support informal caregivers and their care recipients. Personalization can be achieved by linking various psychological, environmental, and lifestyle characteristics to relevant and preferred caregiving solutions (e.g., medication management, treatment adherence, self-care). Informal caregiving places individuals under considerable stress, potentially leading to a host of poor mental and physical health problems. The personalized health application can be understood as a living document tracking an individual's caregiving journey that can be continually updated as circumstances and experiences grow and change. In various embodiments, implementing solution personalization, includes using various algorithms involving machine learning and deep learning methods, natural language processing techniques, and/or a collection of behavioral and observational data that can be used to help better understand an individual's unique contexts and situations, and how those relate to better mental and physical health as well as a better quality of life for the individual.

In at least one embodiment, upon first login, informal caregivers are prompted to complete an intake assessment that gathers information for initial personalization. This personalization can be based on data previously collected through a series of surveys. In at least one embodiment, a series of three surveys is used to establish an initial personalization, any, or all of which can be presented to the user during the first login. At each subsequent login, informal caregivers can be prompted to complete a quick, e.g. one-item, mood/stress assessment as well as to log daily activities including their own personal activities as well as those that involve their care recipient.

The application can also include modules for medication management, treatment adherence, support for activities of daily living (e.g., online shopping, prescription refill, dinner delivery, transportation options), self-care monitoring, caregiver communities, and educational and training resources. As informal caregivers enter content into these modules, complete educational and training resources, and as the application automatically monitors, schedules, and tracks this content, personalization algorithms can continuously run in the background to enable the application to efficiently and effectively deliver recommendations, content, and support to caregivers.

Personalization characteristics include the following:

Caregiver and care recipient demographics: age, gender, race, conditions requiring care, perceived level of need, activities, instrumental activities, and medical/nursing activities needed by care recipient.

Caregiver cultural assessment: caregivers are asked to identify the reasons for being someone's caregiver and to identify their own core values. These variables can be used to identify relatively homogenous caregiver typologies. These typologies represent important ways to personalize the application so that it can provide the best and most preferred resources and materials for each caregiver. Previous research indicates that a person's motivations for caring affect the sustainability of their caregiving including degree of burnout, mental and physical health outcomes, and care recipient quality of life.

Mental health: upon enrollment, caregivers can complete a baseline mental health assessment, which in one embodiment includes using two standard screening devices (the PHQ2 and the GAD2). These two measures include cut scores that indicate whether or not the person is exhibiting behavior consistent with a clinical diagnosis of depression or generalized anxiety. In various embodiments, a "burnout scale" that tracks emotional and physical burnout symptoms can also be used. Finally, daily logins can feature an assessment, which can include a single item in some embodiments, using a picture scale adapted from empirical research, indicating how the user is feeling at a specific point in time. When mental health indices indicate high levels of stress, a series of nudges can be implemented to encourage the caregiver to engage in activities to reduce stress levels. For example, caregivers with a high need for cognition may prefer nudges that are information-based, and thus the application can present information-based nudges upon determining that a caregiver with a high need for cognition is registering high levels of stress.

Physical health: a baseline set of questions regarding physical health can be included in the intake assessment. The application can also monitor and solicit data when relevant on appointments and other relevant information (including sensor data in some embodiments) that suggest changes in physical health that should be closely considered.

Financial health: a baseline set of questions regarding financial health can be included in the intake assessment. As time spent in the application accumulates, a running tally of money saved can be provided to caregivers. In addition, the application can make suggestions about other ways to save money. There are also questions in the cultural assessment that examine the degree to which caregiving is linked to economic motivations.

Appraisal of caregiving burden: a baseline set of items that examines caregivers' subjective appraisal of the burden of caregiving can be included in the intake assessment. The objective burden associated with caregiving (i.e., number of activities of daily living required, number of hours per week, number of years total caregiving) can be exacerbated or minimized based on a caregiver's subjective appraisal of that objective burden. Cultural factors play a large role in a caregiver's subjective appraisal as well. Personalization efforts can also be made using appraisal of subjective burden in combination with cultural factors.

Coping and supports: a baseline set of items that examine coping skills and available social supports can be collected at baseline and periodically updated to reflect waxing and waning caregiver resources. When coping is compromised or social supports unavailable, the application can make recommendations that suggest caregivers pay attention to these variables (e.g., suggest making connections to other caregivers inside the app).

Educational and training resources: the application can track the type and preferred modality used to access educational and training resources as a way to make recommendations and content suggestions. These can also be tailored via other psychological, environmental, and lifestyle characteristics.

In various embodiments, multiple culturally-derived patterns of caregiving identified through a series of surveys administered to informal caregivers can be employed. These patterns, or constructs, include, but are not limited to the following: out of obligation, for economic reasons, due to strong emotional bonds, religious and familial reasons (e.g., duty-bound), cultural reasons, and circumstantial reasons. Each caregiver can fall somewhere along a continuum for each construct. Their position on these continua is then differentially related to message preferences (e.g., cognitive- or affective-framed messages), nudge preferences (e.g., commitment, automatic scheduling), resource preferences (e.g., community support, learning modules), and modality preferences (e.g., reading articles, watching videos, listening to podcasts).

In some embodiments, profiles of caregivers can be derived from attitudes toward a number of well-established cultural indicators (e.g., individualism, collectivism, low vs. high power distance, mono- vs. poly-chronic time). These indicators can then be linked to the caregiving patterns discussed above, to a number of important demographic (e.g., gender, income, living situation) and psychological (e.g., motivations, coping skills, appraisal of caregiving burden) correlates. These cultural indicators coupled with the caregiving patterns and the demographic and psychological correlates can be used to identify which nudges, resources, messages, and modalities caregivers prefer. This analysis allows us to create personalized medicine interventions via a mobile health app.

Referring to FIG. 1, a method of generating a personalized graphical user interface (GUI) can be discussed in accordance with embodiments of the present disclosure. Various embodiments disclosed herein employ a graphical user interface (GUI). A method of generating a graphical user interface (GUI) for a health-related application includes: receiving a user request to log in to a session of the health-related application 101; obtaining user characteristic information, wherein the user characteristic information includes one or more of user psychological information, user environmental information, or user lifestyle information 103; selecting particular GUI elements to be presented to the user during the session, wherein the particular GUI elements are selected based on the user characteristic information 104; generating a personalized GUI including the particular GUI elements 105; and transmitting the personalized GUI to a user device for display during the session 107.

The method discussed above can further include obtaining initial user characteristic information using an intake assessment. In some such embodiments, the intake assessment is presented using a default GUI including default GUI elements. In some embodiments, the intake assessment includes information entered by an interviewer during an on-line interview. Any or all of the methods of generating the GUI can include obtaining additional user characteristic information during subsequent sessions and selecting updated particular GUI elements for display to the user during the subsequent sessions based on the user characteristic information and the additional user characteristic information. In various implementations, the user characteristic information includes one or more of the following: caregiver and care recipient demographics, caregiver cultural background, caregiver mental health rating, caregiver physical health rating, caregiver financial health rating, caregiver perceived burden rating, caregiver object burden rating, caregiver coping skills rating, caregiver social support rating; caregiver preferred modality for receiving educational and training resources.

Figure 2:
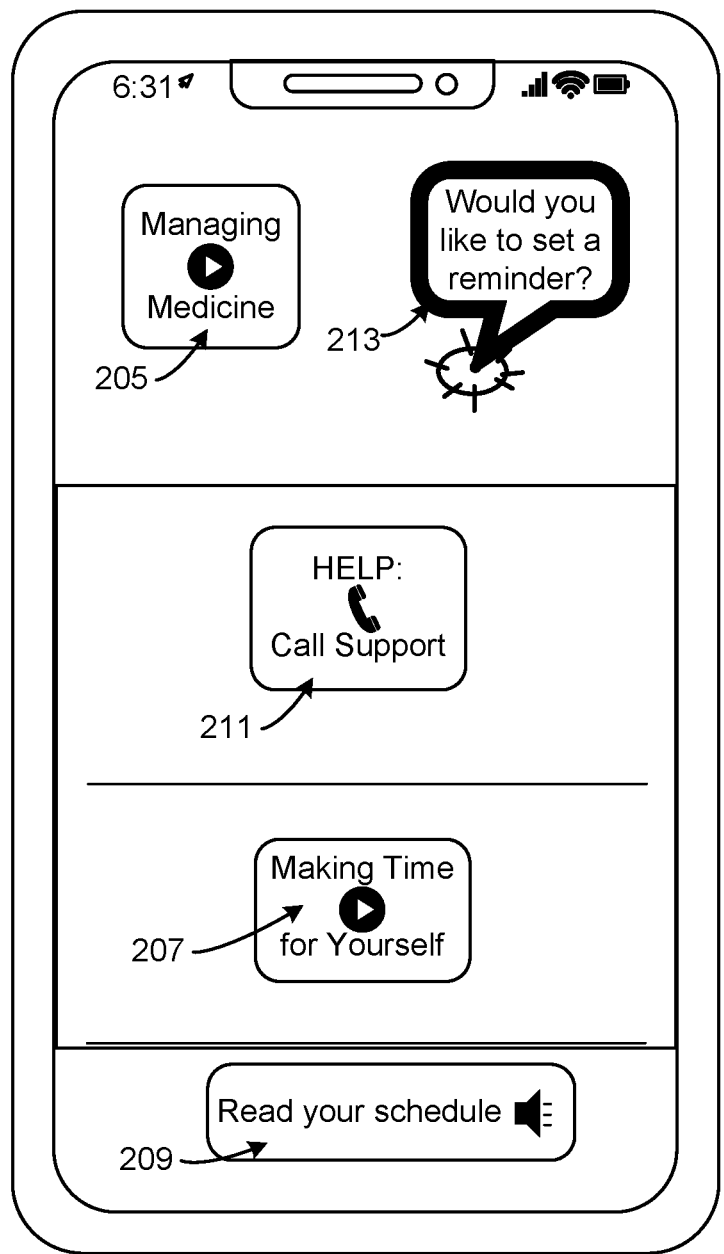
FIG. 2 is a diagram of a GUI displaying information based on caregiver characteristics that indicate a preference for auditory information, in accordance with embodiments of the present disclosure.

Referring next to FIG. 2 a GUI 200 displaying information based on caregiver characteristics that indicate a preference for auditory information can be discussed in accordance with embodiments of the present disclosure. GUI 200 displays first user selectable object 205 that can be selected to initiate playout of an audio or audio-visual podcast entitled "Managing Medicine." GUI 200 also displays second user selectable object 207 that can be selected to initiate playout of an audio or audio-visual podcast entitled "Making time for yourself." Upon selection, user selectable object 209 will activate readout of the caregiver's schedule. Activation of fourth user selectable object 211 initiates an audio call to a preconfigured support number. Speaker 213 is illustrated as providing an audible question asking the caregiver or user of the health application whether they would like to set a reminder. In response to the query, the user can verbally respond to set a reminder if desired.

Because GUI 200 is presenting information to a user that prefers to receive and provide information audibly, various text to speech and speech to text techniques can be used to update and present the caregiver's calendar, preferences, or the like. In some embodiments, playout of podcasts can be controlled using voice commands. Note that even though GUI 200 is personalized for a caregiver that prefers to interact audibly, options for visual and/or tactile interaction can also be presented for times when the caregiver desires privacy. Also note that the information can be transmitted to earbuds, headsets, or other devices, depending on user setting within the healthcare application or global settings of the caregiver's handheld device. Also note that for caregivers that favor audible communication, but are not at the extreme end of the audible preference spectrum, a mix of information items can be displayed based on the caregiver characteristics.

Figure 3:
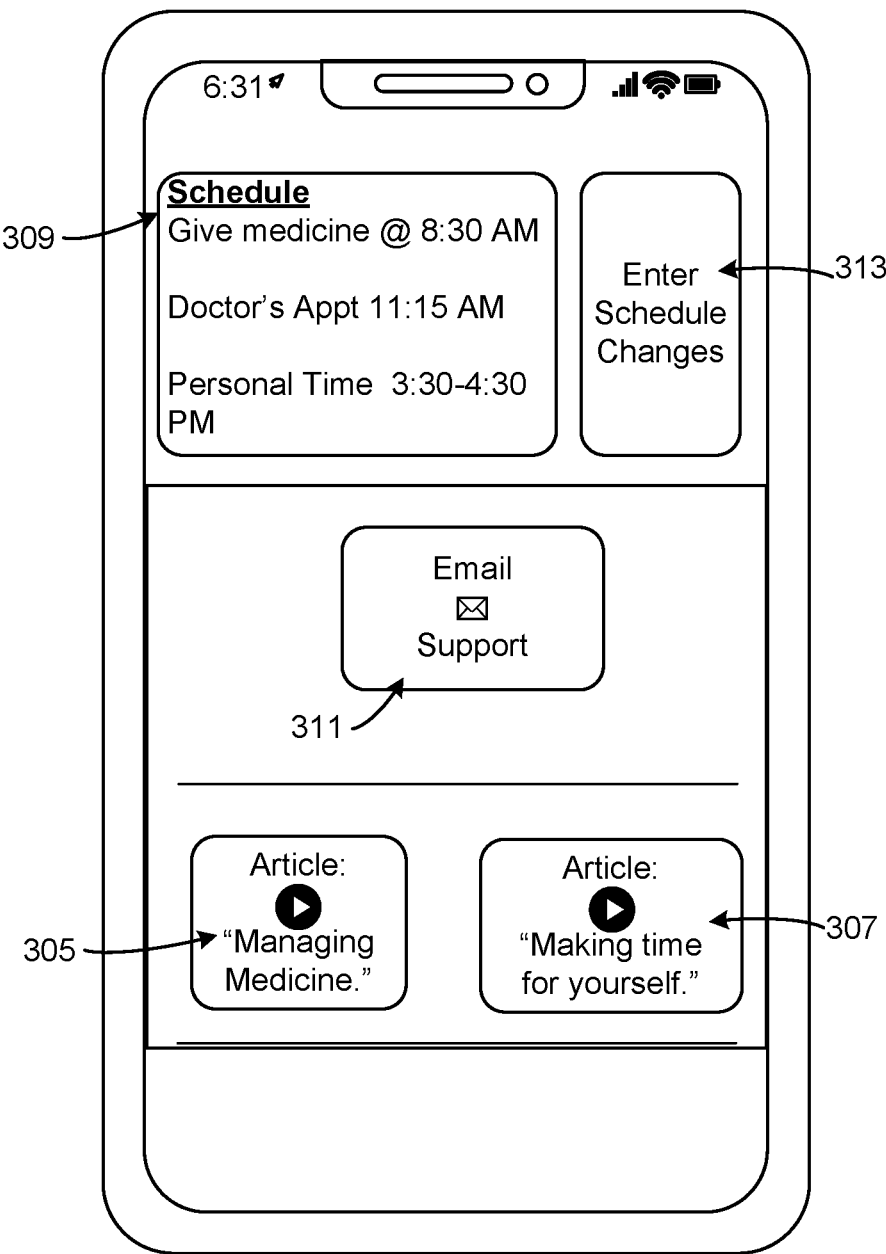
FIG. 3 is a diagram of a GUI displaying information based on caregiver characteristics that indicate a preference for textual or visual information, in accordance with embodiments of the present disclosure.

Referring next to FIG. 3 a GUI 300 displaying information based on caregiver characteristics that indicate a preference for visual/textual information will be discussed in accordance with embodiments of the present disclosure. GUI 300 displays fifth user selectable object 305 that can be selected to initiate display of a text article entitled "Managing Medicine." GUI 300 also displays sixth user selectable object 307 that can be selected to initiate display of a text article entitled "Making time for yourself." Object 309 displays a text/visual version of the caregiver's schedule. Seventh user selectable object 311 initiates a text chat with email support, Eight user selectable object 313 can be selected to allow the caregiver to make text changes to their schedule.

Although not specifically illustrated in FIGS. 2 and 3, either GUI can be used to display "nudges" on a periodic basis, in response to occurrence of a calendar event, in response to starting, stopping, pausing, displaying, or otherwise interacting with an item of information presented on the GUIs. These nudges can be audible, visual, textual, or tactile prompts, alerts, questions, suggestions, or the like.

Figure 4:
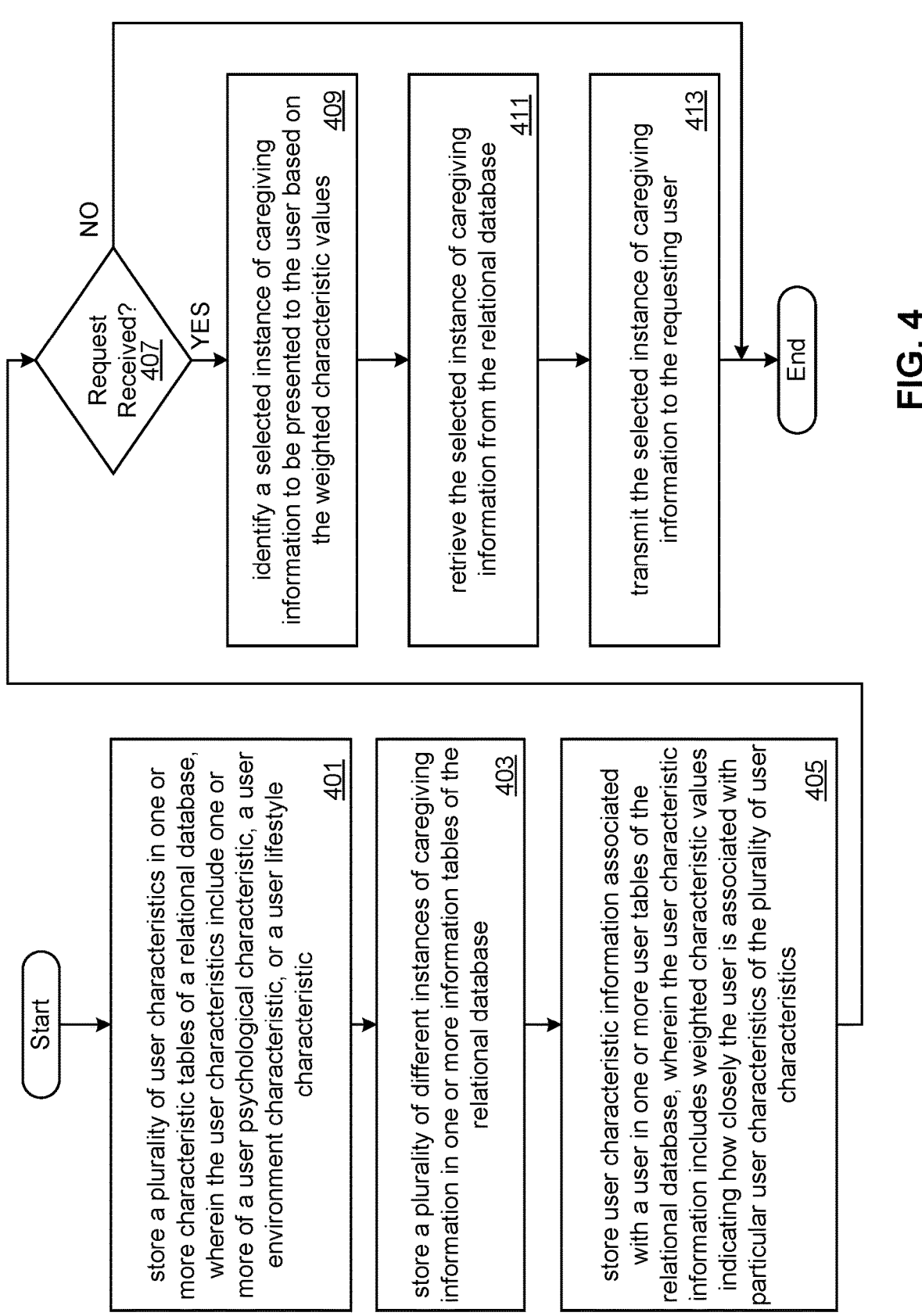
FIG. 4 is a flow diagram illustrating a method of providing caregiving information in accordance with embodiments of the present disclosure.

Referring next to FIG. 4, a method of providing caregiving information will be discussed in accordance with embodiments of the present disclosure. Some embodiments can be implemented using a database. One such embodiment is a method of providing caregiving information, the method comprising: storing a plurality of user characteristics in one or more characteristic tables of a database, wherein the user characteristics include one or more of a user psychological characteristic, a user environment characteristic, or a user lifestyle characteristic 401; storing a plurality of different instances of caregiving information in one or more information tables of the database 403; storing user characteristic information associated with a user in one or more user tables of the database, wherein the user characteristic information includes weighted characteristic values indicating how closely the user is associated with particular user characteristics of the plurality of user characteristics 405; in response to receiving a request for the caregiving information from a requesting user 407: identifying a selected instance of caregiving information to be presented to the user based on the weighted characteristic values 409; retrieving the selected instance of caregiving information from the database 411; and transmitting the selected instance of caregiving information to the requesting user 413.

In various embodiments, including any of the methods discussed above, a first of the plurality of different instances of caregiving information includes first information configured for presentation in a first modality and first information configured for presentation in a second modality. In one such implementation, the first modality and the second modality are selected from the group consisting of written articles, video content, and auditory content.

In the above, and in other embodiments, the plurality of different instances of caregiving information includes one or more of links to community resources, instructional items, inspirational items, quizzes, nudges, reminders, games, or resource contact information. In various embodiments, automated alteration of default communication methods based on multiple stages of user input are performed.

Referring next to FIG. 5 a method of determining user preferences will be discussed in accordance with embodiments of the present disclosure. A method comprises: receiving, at a server device, an initial user login request from a user, wherein the initial login request includes a request to access a health-related application 501; in response to receiving the initial user login request, presenting an intake assessment to the user 503; generating a current user profile based, at least in part, on the intake assessment 505; receiving, over time, a plurality of additional user login requests from the user 506; iteratively, for each of the plurality of additional login requests: presenting selected information to the user based at least in part on the current user profile 507; presenting an additional assessment item to the user 509; receiving a response to the additional assessment item 511; updating the current user profile to reflect the response to the additional assessment item 513.

In any of the above implementations, receiving a response to the additional assessment item includes: analyzing response parameters, wherein the response parameters include one or more of evaluating language used in the a response, determining a response modality, determining an elapsed time between presentation of the additional assessment item and a time the response is generated, evaluating consistency between the response to the additional assessment item and responses to previously presented assessment items; determining a number of assessment items that result in any response, determining how many assessment items presented result in responses, a time of day associated with the response, a time elapsed since a previous login, or a number of assessment items previously presented.

Various methods also include presenting selected information to the user based at least in part on the analyzing, and/or selecting a number of items to present to the user based on the analyzing. In some embodiments, presenting an additional assessment item to the user includes selecting a number of items to present to the user based on the current user profile.

Referring next to FIG. 6 a method employing machine learning/artificial intelligence in accordance with embodiments of the present disclosure. In addition to, or in place of using a database to implement various embodiments, artificial intelligence (AI) techniques can be used. In one or more embodiments, a method comprises: obtaining information indicating information consumption preferences associated with caregivers 601; obtaining caregiver characteristics of the caregivers 603; providing the information indicating information consumption preferences associated with the caregivers and the caregiver characteristics of the caregivers as training information to a machine learning module being executed on a processing device 605, wherein the machine learning module is configured to train itself by: performing first comparisons of individual information consumption preferences of individual caregivers to the caregiver characteristics associated with the individual caregivers 607; establishing first links between caregiver characteristics and information consumption preferences based on the first comparisons 609; performing second comparisons of sets of information consumption preferences of the individual caregivers to sets of caregiver characteristics associated with the individual caregivers 611; establishing second links between sets of caregiver characteristics information and consumption preferences based on the second comparison 613; obtaining additional caregiver characteristics of an additional caregiver 615; providing the caregiver characteristics of the caregivers as input to be evaluated by the machine learning module being executed on the processing device 617, wherein the machine learning module is configured to: evaluate the additional caregiver characteristics to identify likely information consumption preferences of the additional caregiver 619; establish one or more learned links between the additional caregiver and one or more items of information conforming to the likely information consumption preferences of the additional caregiver 621; and updating the first links and the second links based on the learned links 623.

The method above can further include using the machine learning module to identify patterns of caregiving based on culturally derived patterns of caregiving associated with the caregiver. In one or more of the methods disclosed herein, the culturally derived patterns of caregiving include one or more of caregiver perceived obligations, caregiver economic resources, caregiver emotional bonds, caregiver perceived religious obligations, caregiver perceived familial obligations, and caregiver perceived circumstances.

Some such methods also include using the machine learning module to assign weighted values to the first links and the second links, wherein a maximum weighted value and a minimum weighted value define a continuum, and an assigned value designates a location along the continuum.

Referring next to FIG. 7, a method of using a caregiver profile will be discussed in accordance with embodiments of the present disclosure. Any or all of the above embodiments can include the use of caregiver or user profiles. A method according to some embodiments includes: establishing a caregiver profile associated with a caregiver 701; storing a plurality of information items associated with particular cultural attitudes 703; linking one or more cultural identifiers to each of the plurality of information items 705; presenting a series of cultural indicators to a caregiver 707; obtaining from the caregiver, responses to the series of cultural indicators, wherein the responses indicate attitudes of the caregiver towards the cultural indicator 709; evaluating the responses to determine a cultural identifier most closely matching the attitudes of the caregiver 711; establishing one or more links between the caregiver profile and information items linked to the cultural identifier most closely matching the attitudes of the caregiver 713; and providing information to the caregiver based on the caregiver profile 715.

In some of the above disclosed embodiments, the cultural attitudes include individualism, collectivism, low vs. high power distance, mono- vs. poly-chronic time. Optionally, various methods disclosed herein include establishing one or more links between the caregiver profile and a cultural caregiving pattern.

Referring next to FIG. 8, a flow diagram illustrating a method for use in a system will be discussed in accordance with embodiments of the present disclosure. In one embodiment, a system comprises: a processor; memory coupled to the processor; a program of instructions stored in the memory and executed by the processor, the program of instructions including: at least one instruction to infer caregiving characteristics of a user based on user interactions within a personalized health application 801; at least one instruction to store a caregiver profile in the memory, wherein the caregiver profile includes a plurality of the caregiving characteristics 803; at least one instruction to select one or more caregiving solutions based, at least in part, on the caregiver profile 805; and at least one instruction to provide, from within the personalized health application, information associated with the one or more caregiving solutions to the user 807.

The caregiving characteristics of the user optionally include one or more of the following: psychological characteristics, environmental characteristics, or lifestyle characteristics. The one or more caregiving solutions optionally include medication management, treatment adherence, or self-care.

Figure 9:
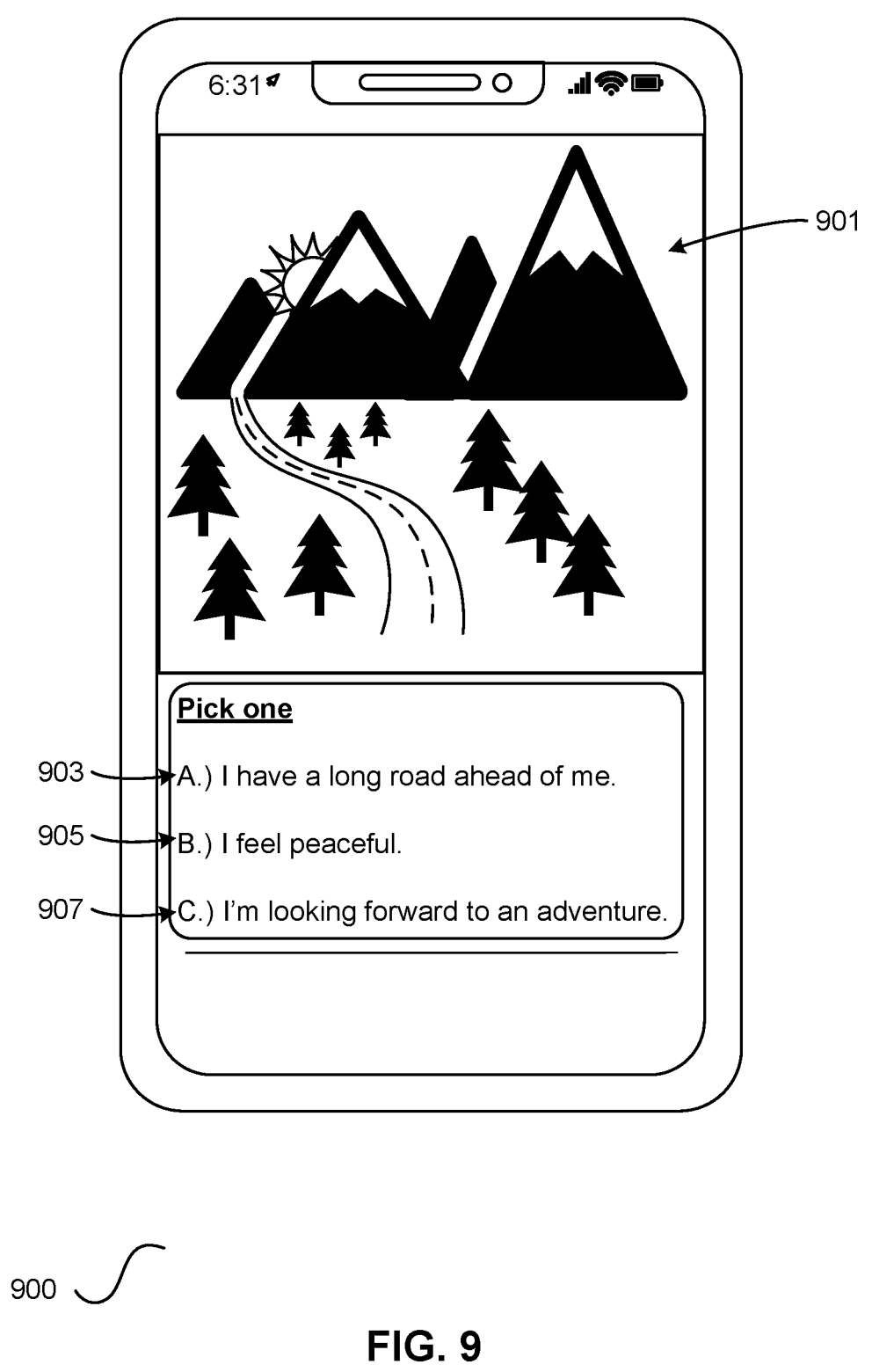

Referring next to FIG. 9, a one-question mood assessment is illustrated in accordance with embodiments of the present disclosure. As illustrated, a picture 901 can be presented within the GUI of a healthcare application in accordance with the present disclosure. In conjunction with the picture, options can be presented visually or audibly to the caregiver, and the caregiver can be invited to select the option that most closely matches the caregiver's reaction to the picture. For example, option A 903 asks whether the caregiver reacts to the picture by feeling that "I have a long road ahead of me," option B 905 asks if the picture makes the caregiver feel peaceful, and option C 907 asks if the picture makes the caregiver feel as if they are looking forward to an adventure.

The caregiver's response can be added to the caregiver profile associated with the caregiver and be used as input into an algorithm that determines which type of information should be provided to the caregiver. Selection of information types is not limited to modalities, e.g., visual, text, audible, or some combination thereof. Instead, selection of information can also include selection of inspirational content, encouragement content, self-care suggestions, training, suggestions regarding how best to care for another person, professional referrals, or the like.

Figure 10:
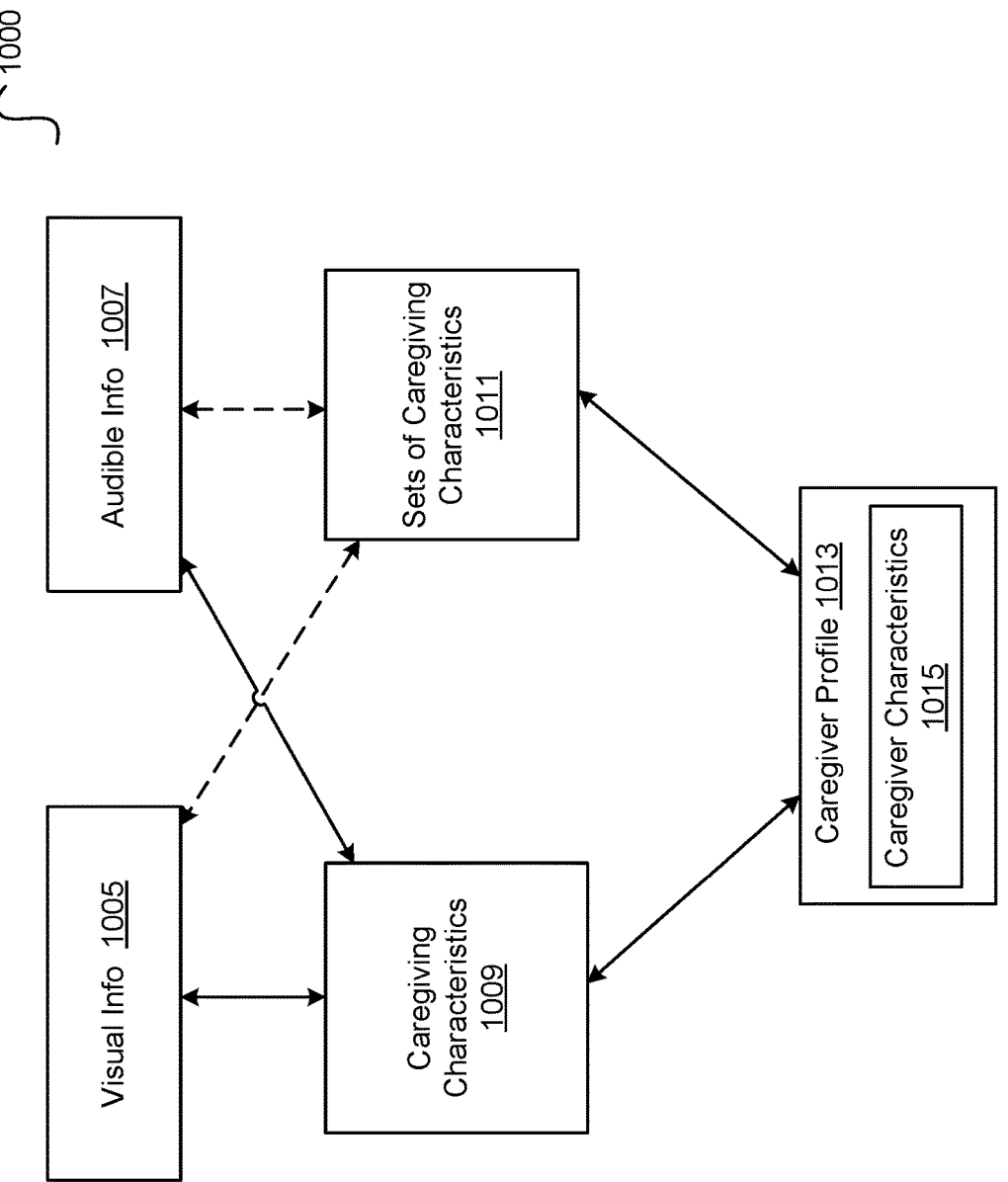
FIG. 10 is a diagram illustrating a data construct in accordance with embodiments of the present disclosure.

Referring next to FIG. 10 a data construct 1000 will be discussed in accordance with embodiments of the present disclosure. Data construct 1000 illustrates a database structure that includes table 1005 storing visual caregiving information files, or pointer to visual caregiving information, such as files in MP4, MOV, WMV, AVI, AVCHD, FLV, or F4V formats. Table 1007 stores audible caregiving information files, or pointers to audio caregiving information, such as files in WAV, AIFF, AU, MP3 formats. The information in table 1005 and table 1007 is linked to individual caregiving characteristics via table 1009, and to sets of caregiving characteristics via table 1011. Caregiver profile 1013, is linked to visual information or audible information based on caregiver characteristics 1015 included in caregiver profile 1013.

Figure 11:
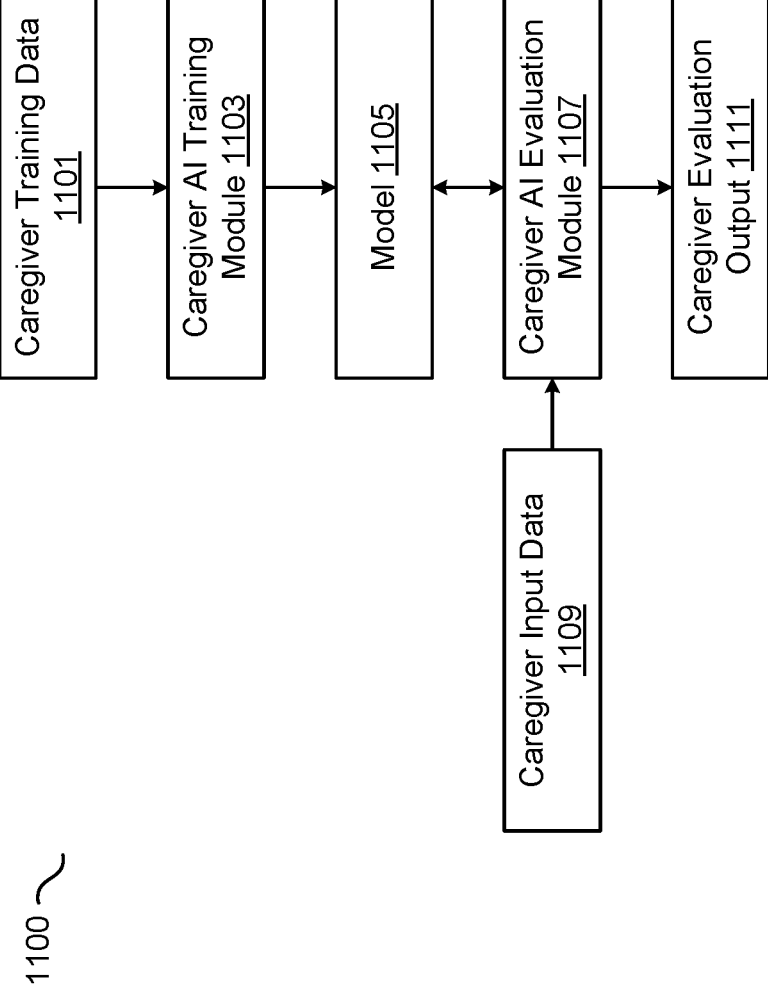
FIG. 11 is a diagram illustrating a machine learning/AI system in accordance with embodiments of the present disclosure.

Referring next to FIG. 11, a machine learning/AI system 1100 will be discussed in accordance with embodiments of the present disclosure. Machine learning/AI system 1100 includes caregiver training data 1101, caregiver AI training module 1103, model 1105, caregiver AI evaluation module 1107, caregiver input data 1109, and caregiver evaluation output 1111.

Caregiver training data 1101 may include information containing known relationships between caregiver characteristics and preferred information and is provided as input to caregiver AI training module 1103. Caregiver AI training module 1103 can process some or all of the caregiver training data 1101 and identify relationships, patterns, etc. in caregiver training data 1101. The caregiver AI training module 1103 may then output a model 1105 that represents the identified relationships, patterns, etc. The caregiver AI evaluation module 1107 may then provide caregiver input data 1109 to model 1105 and then output caregiver evaluation output 1111 based, at least in part, on the output of the model 1105.

The caregiver training data 1101 may vary depending on the implementation. In some implementations the caregiver training data may comprise one or more characteristics associated with a caregiver or caregivers that have a relationship to one or more information preferences for the caregiver(s). For example, the input data might include answers to survey questions designed to determine what type of caregiver the caregivers are and whether they prefer information to be presented in audio or visual form.

Machine learning/AI systems can implement a variety of different machine learning or AI techniques, including decision trees, neural networks, etc. As such, caregiver AI training module 1103 may implement one or more machine learning or AI techniques and the model 1105 output by the caregiver AI training module can vary accordingly. The model 1105 may include, specify, or perform operations that involve cleaning, preparing, or otherwise transforming any input data (e.g., caregiver training data 1101).

The caregiver input data 1109 may vary depending on the implementation. In many implementations, however, the caregiver input data 1109 will contain a subset of the caregiver training data 1101. For example, if the caregiver training data 1101 comprises one or more characteristics associated with a caregiver or caregivers that have a relationship to one or more information preferences for the caregiver(s), the caregiver input data 1109 may be one or more characteristics associated with a particular caregiver.

Because the caregiver AI evaluation module 1107 is designed to work with the model 1105, the caregiver AI evaluation module 1107 may vary according to the particular type of machine learning/AI techniques implemented.

The caregiver evaluation output 1111 may vary between implementations. In many implementations, however, the caregiver evaluation output 1111 will contain the subset of the caregiver training data 1101 not included in the caregiver input data 1109. For example, if the caregiver training data 1101 comprises one or more characteristics associated with a caregiver or caregivers that have a relationship to one or more information preferences for the caregiver(s) and the caregiver input data 1109 is the one or more characteristics associated with a particular caregiver, then the caregiver evaluation output 1111 might be one or more information preferences for a caregiver associated with the caregiver input data 1109.

Figure 12:
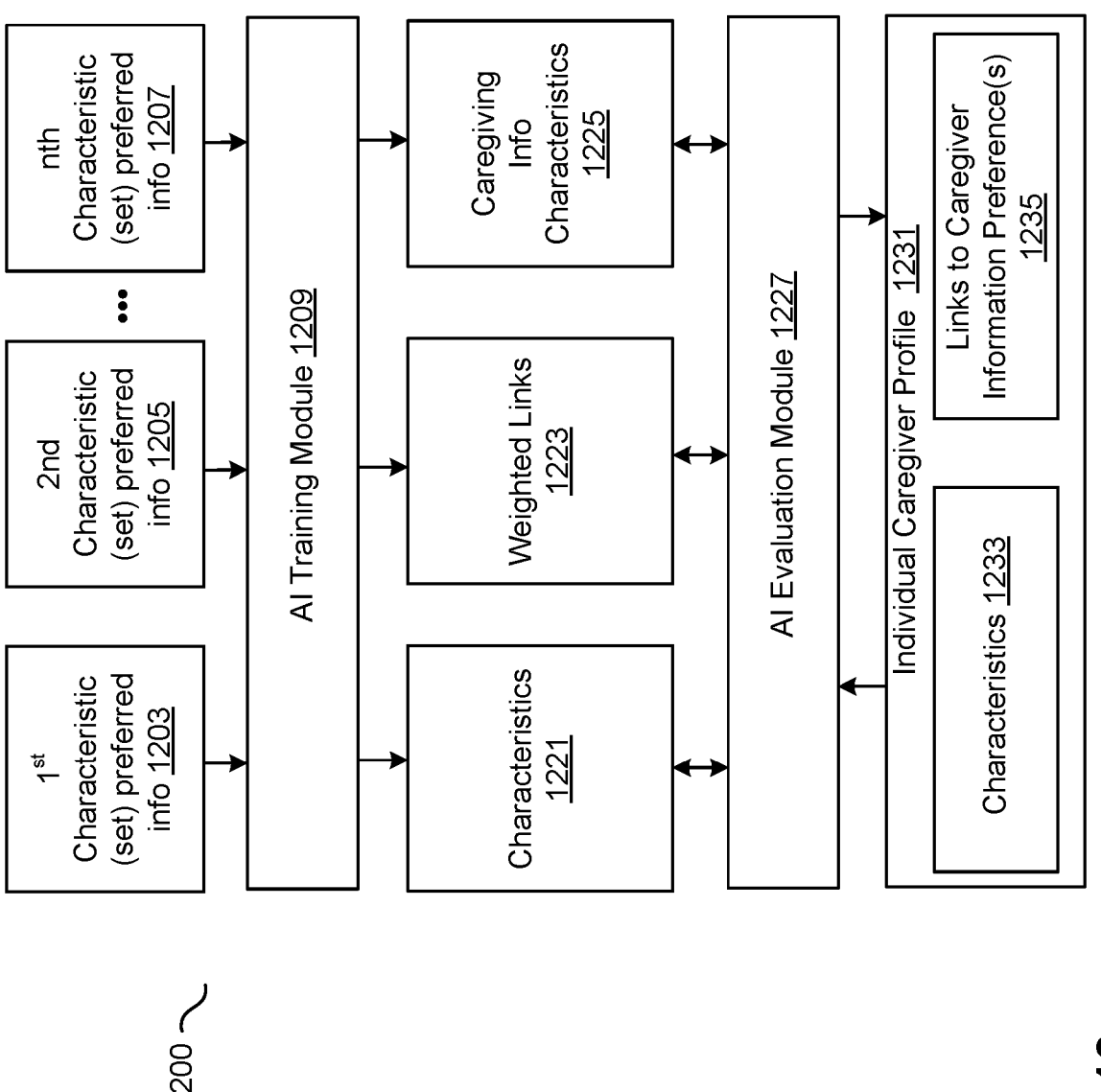
FIG. 12 is a diagram illustrating a machine learning/AI system in accordance with embodiments of the present disclosure.

Referring next to FIG. 12 a machine learning/AI system 1200 will be discussed in accordance with embodiments of the present disclosure. Machine learning/AI system 1200 includes AI training module 1209 and AI evaluation module 1227. Training information having known relationships between caregiver characteristics and preferred information is provided as input to AI training module 1209.

In the illustrated example, first training information 1203 includes a $1^{st}$ characteristic, or set of characteristics, having a known relationship to first information preferences of a first caregiver. Second training information 1205 includes a $2^{nd}$ characteristic, or set of $2^{nd}$ characteristics, having a known relationship to second information preferences of a second caregiver. Similarly, $n^{th}$ training information 1207 includes an $n^{th}$ characteristic, or set of $n^{th}$ characteristics, having a known relationship to $n^{th}$ information preferences of an $n^{th}$ caregiver.

The training information is use by AI training module 1209 to train machine learning/AI system 1200. For example, in at least one embodiment, AI training module 1209 uses the training information to generate characteristic table 1221, which includes characteristics and/or sets of characteristics included in the training information. AI training module 1209 can also generate caregiving information characteristics table 1225, which can include characteristics associated with the information preferences included in the training information.

In various embodiments, AI training module 1209 iteratively compares the known relationships included in the training information, and can generated weighted links table 1223, which includes link values determined based on correspondences among the various characteristics and information preferences. For example, if an analysis of the training data indicates that all caregivers having a characteristic A have an information preference B, which indicates that the caregiver prefers to receive schedule reminders at a set time each day, the weighting value applied to a link between characteristic A and information preference B can be set to 1, which represents a 100% correspondence.

Conversely, if an analysis of the training data indicates that no caregivers having a characteristic X have information preference B, the weighting value applied to a link between characteristic X and information preference B can be set to 0, which represents a null correspondence. Various weighting values can represent any value along a continuum from no correspondence to full correspondence. The weighted links can be links between any single caregiver characteristic or combination/set of caregiver characteristics to any single information characteristic or combination/set of caregiver characteristics.

When deciding what information to provide to a user of the health application, AI evaluation module 1227 can obtain caregiver characteristics table 1233 from a caregiver profile 1231 associated with the caregiver and determine weighted links between the caregiver characteristics table 1233 and information characteristics stored in caregiving information characteristics table 1225. The determination can be based on the information stored by AI training module 1209 in the characteristics table 1221, weighted links table 1223, and caregiving information characteristics table 1225. The links determined by AI evaluation module 1227 can be stored in links to caregiver information preferences 1235 in caregiver profile 1231.

Machine learning/AI system 1200 is an example of the machine learning/AI system 1100, with the caregiver training data 1101 comprising first training information 1203, second training information 1205, and $n^{th}$ training information 1207, the caregiver input data 1109 comprising the caregiver characteristics stored in caregiver characteristics table 1233, and the caregiver evaluation output 1111 comprising the links to caregiver information preferences 1235.

Figure 13:
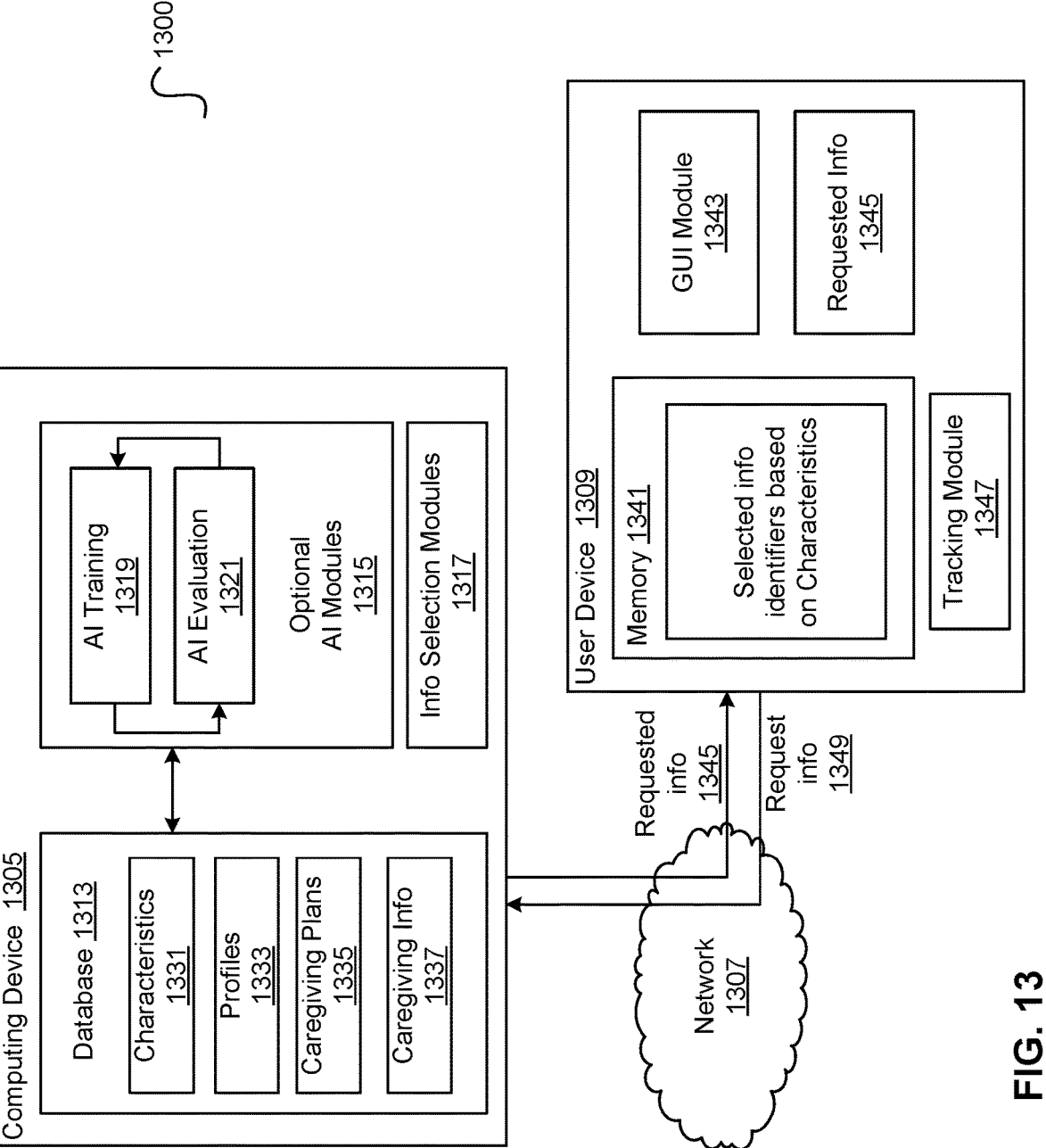
FIG. 13 is a diagram illustrating a system in accordance with embodiments of the present disclosure.

Referring next to FIG. 13 a system will be discussed in accordance with embodiments of the present disclosure. System 1300 includes computing device 1305 coupled to user device 1309 via communication network 1307. Computing device 1305 includes database 1313 which stores characteristics 1331, profiles 1333, caregiving plans 1335, caregiving information 1337, and/or links or pointers to those and other items. Computing device 1305 also includes information selection modules 1317. Computing device 1305 further includes optional AI modules 1315, including AI training module 1319 and AI evaluation module 1321.

User device 1309 includes memory 1341, which stores selected information identifiers that have been selected based on caregiver characteristics. User device 1309 also includes a GUI module 1343, storage for requested information 1345, and an optional tracking module 1347, which can be used to obtain information used to update a caregiver profile. In various embodiments, user device 1309 is used to execute a healthcare application which uses the information stored on user device 1309 to select and display information to the caregiver in accordance with inferred or specified caregiver preferences.

For example, computing device 1305 can use information selection modules 1317 to evaluate caregiver characteristics included in a profile stored at computing device 1305 or locally on user device 1309 and provide information identifiers to user device 1309. The information identifiers can include addresses from which particular information can be obtained, type identifiers, modality identifiers, filenames, weighted links, or the like. In some embodiments, the healthcare application running on user device 1309 transmits a request for information 1349 to computing device 1305 via communication network 1307. Computing device 1305 can service the request, forward the request to another computing device for servicing, or the like. In any case, the requested information 1345 can be returned to user device 1309 for use in providing information customized according to caregiver preferences—either inferred or specified.

In various embodiments, some or all of the requested information can be pre-loaded and stored on user device 1309 to allow operation of the application without network connectivity. In other embodiments, the requested information is streamed or otherwise provided to user device 1309 contemporaneously with the request.

Figure 14:
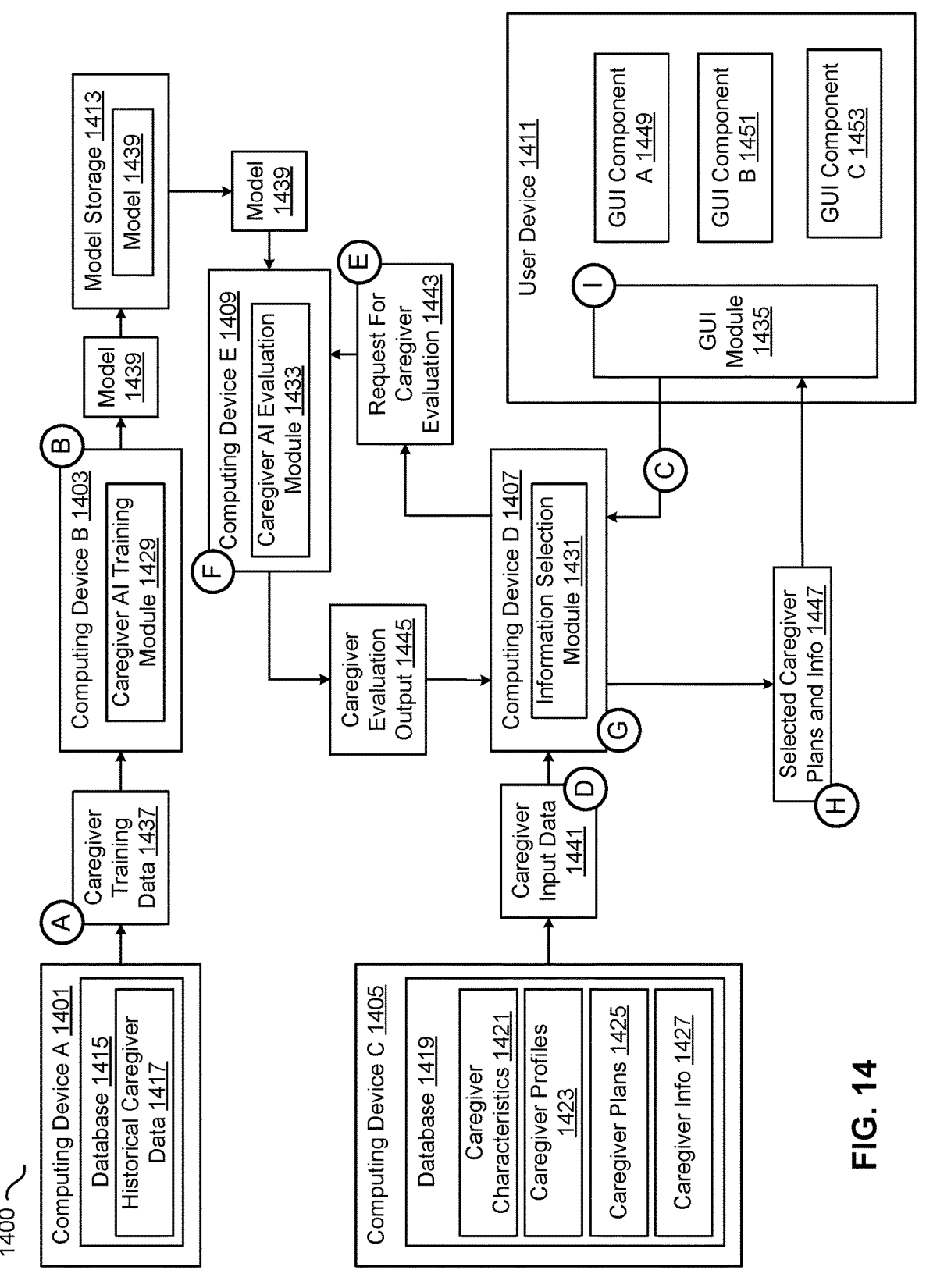
FIG. 14 is a diagram illustrating a system in accordance with embodiments of the present disclosure.

Referring now to FIG. 14, an example system will be discussed in accordance with embodiments of the present disclosure. System 1400 includes computing device A 1401, computing device B 1403, computing device C 1405, computing device D 1407, and computing device E 1409. System 1400 also includes user device 1411 and model storage 1413.

Computing device A 1401 includes database 1415, which includes historical caregiver data 1417. Computing device C 1405 may include caregiver-related data, including caregiver characteristics 1421, caregiver profiles 1423, caregiver plans 1425, and caregiver information 1427. The historical caregiver data 1417 may include caregiver characteristics, caregiver profiles, caregiver plans, and caregiver info similar to the caregiver-related data in database 1419 and may also include indications of links, patterns, or relationships between the caregiver-related data and caregiver information preferences.

Computing device B 1403 includes caregiver AI training module 1429, computing device D 1407 includes information selection module 1431, and computing device E 1409 includes caregiver AI evaluation module 1433. User device 1411 includes GUI module 1435.

The computing devices and other components of system 1400 operate together to implement the processes and techniques described herein and example operations are described below.

At stage A, caregiver training data 1437 is provided to the caregiver AI training module 1429. The providing of caregiver training data 1437 to caregiver AI training module 1429 can be provided via a push mechanism or pull mechanism and can be triggered by computing device A 1401, computing device B 1403, another computing device, or any appropriate mechanism. The operations corresponding to Stage A may be executed periodically (e.g., on a schedule) or may be executed on an as-needed basis.

At stage B, caregiver AI training module 1429 analyzes caregiver training data 1437 and generates model 1439, saving model 1439 to model storage 1413. As described above, model 1439 can be a single model, multiple models, etc. Model storage 1413 can be any kind of persistent storage usable to save model 1439, including a hard drive, cloud storage, etc.

At stage C, the GUI module 1435 sends, to the information selection module 1431, a request for caregiving plans or information corresponding to a user logged into user device 1411. The request may indicate that the user has opened a particular section of an application, has specifically requested certain information, etc. The request may also include metadata about the user, such as metadata identifying the user, updated caregiver profile information or caregiver characteristics, etc.

At stage D, the information selection module 1431 retrieves the caregiver input data 1441. The caregiver input data 1441 can vary between information, but generally includes data from the caregiver characteristics 1421 and caregiver profiles 1423 that correspond to the user logged into the user device 1411. For example, the caregiver input data 1441 might include responses to various questions used to determine the particular culturally-derived patterns of caregiving the user falls into.

Although depicted as retrieving the caregiver input data 1441 from the computing device C 1405, the source of the caregiver input data 1441 can vary. For example, the caregiver input data 1441 might be part of the request received by the information selection module 1431 at stage C or might be determined by additional interactions with the user device 1411 (e.g., the information selection module 1431 might request that the GUI module 1435 retrieve additional, updated information from the user).

At stage E, the information selection module 1431 sends a request for caregiver evaluation 1443 to caregiver AI evaluation module 1433. The request for caregiver evaluation 1443 can include the caregiver input data 1441.

At stage F, the caregiver AI evaluation module 1433 generates the caregiver evaluation output 1445. To generate the caregiver evaluation output 1445, the caregiver AI evaluation module 1433 applies the model 1439 to the caregiver input data 1441. The caregiver evaluation output 1445 may be the output of the model 1439 or may be the result of performing additional operations on the output of the model 1439.

The caregiver evaluation output 1445 can vary between implementations but generally provides some information usable by the information selection module 1431 to determine what caregiver information should be selected. For example, the caregiver evaluation output 1445 can include links to caregiver information preferences as described in relation to FIG. 12, such as an indication that the caregiver likely prefers information to be presented in an audio format.

At stage G, the information selection module 1431 uses the caregiver evaluation output 1445 to select caregiver plans and information 1447. The particular operations performed to select the caregiver plans and information 1447 may vary between implementations. For example, if the caregiver evaluation output 1445 indicates that the user likely prefers information to be presented in an audio format, the information selection module 1431 may query the database 1419 for caregiver information that is stored in an audio format. If the caregiver information is located in a directly accessible filesystem, the information selection module 1431 may determine a directory in which audio-based information is stored.

At stage H, the information selection module 1431 sends the selected caregiver plans and information 1447 to the GUI module 1435. The selected caregiver plans and information 1447 is just an example of the types of data that might be selected based on the caregiver evaluation output 1445, and the selected caregiver plans and information 1447 may include caregiver plans 1425, caregiver information 1427, a combination thereof, or any other information responsive to the request received at stage C.

The selected caregiver plans and information 1447 may not be sent directly and, instead, links to the selected caregiver plans and information 1447 or similar metadata may be sent. For example, the selected caregiver plans and information 1447 may include uniform resource identifiers, filesystem paths, etc. that point to where the information can be accessed.

At stage I, the GUI module 1435 generates one or more GUI components, such as GUI component A 1449, GUI component B 1451, and GUI component C 1453, based at least in part on the selected caregiver plans and information 1447. For example, if the selected caregiver plans and information contains three videos (or links to videos), the GUI module 1435 may create three GUI components designed to allow the user to watch the videos.

Both system 1300 and system 1400 perform similar operations that implement the techniques described herein. System 1400, however, has various functionalities delegated to different computing devices, as the noted in the description of system 1300. Thus, instead of passing information between components on a single computing device (computing device 1305), system 1400 passes information between separate computing devices.

Utilizing different computing devices for different functionalities (workloads) allows the computing devices to be optimized for the particular functionality. For example, a workload consisting of training a machine learning/AI model may require large amounts of memory but only be performed periodically. On the other hand, a workload consisting of processing requests and sending a query to a database (e.g., as done by the information selection module 1431) may require little memory and may be done frequently. As such, using a single computing device for both types of workloads might require a computing device that had large amounts of memory in order to support the machine learning/AI model training workload, but the memory would sit unused the vast majority of the time. Splitting the workloads, however, might allow for a computing device with large amounts of memory to be provisioned only when needed for the machine learning/AI model training workload while a computing device with lower amounts of memory could be available for servicing requests from user devices at all times.

Similarly, training a machine learning/AI model may require lots of data and may not require a quick response time while responding to user requests may require smaller amounts of data and may require a quick response time. As such, storing the data used for training the machine learning/AI model (e.g., caregiver training data 1437) on a computing device with lower performance and higher latency and the data required to handle user requests (e.g., caregiver profiles 1423) on a higher performance computing device may reduce costs over storing all of the data on a single computing device.

System 1400 is an example and actual implementations can vary. For example, information selection module 1431 may execute on the same computing device as caregiver AI evaluation module 1433. As another example, historical caregiver data 1417 might not be stored on a computing device but may instead be stored in cloud-based object storage.

Another example of a possible implementation of system 1400 is that the GUI module 1435 may execute on a computing device such as computing device D 1407 and transmit the generated GUI components to the user device 1411 (sometimes referred to as "server-side rendering"). This may reduce the load on the user device 1411, improving the user's perception of responsiveness and allowing for use of various caching techniques.

The operations performed may also vary between implementations. For example, the operations performed at stages D and E may only be performed when a caregiver profile corresponding to the user logged into the user device 1411 changes. Thus, instead of applying the model 1439 to the caregiver input data 1441 with every request for information received from the user device 1411, the information selection module 1431 may instead persist the caregiver evaluation output 1445 in database 1419 (e.g., as part of the caregiver profiles 1423) and use the persisted caregiver evaluation output 1445 until the caregiver input data 1441 has changed or a certain amount of time has passed. For example, as noted above, not only can caregivers enter content into various application modules and complete educational and training resources, but the application can automatically monitor, schedule, and track these changes and interactions. When the application detects these changes and interactions, the application may trigger the operations described at stages D through G, allowing updated recommendations, content, and support to delivered to caregivers.

Figure 15:
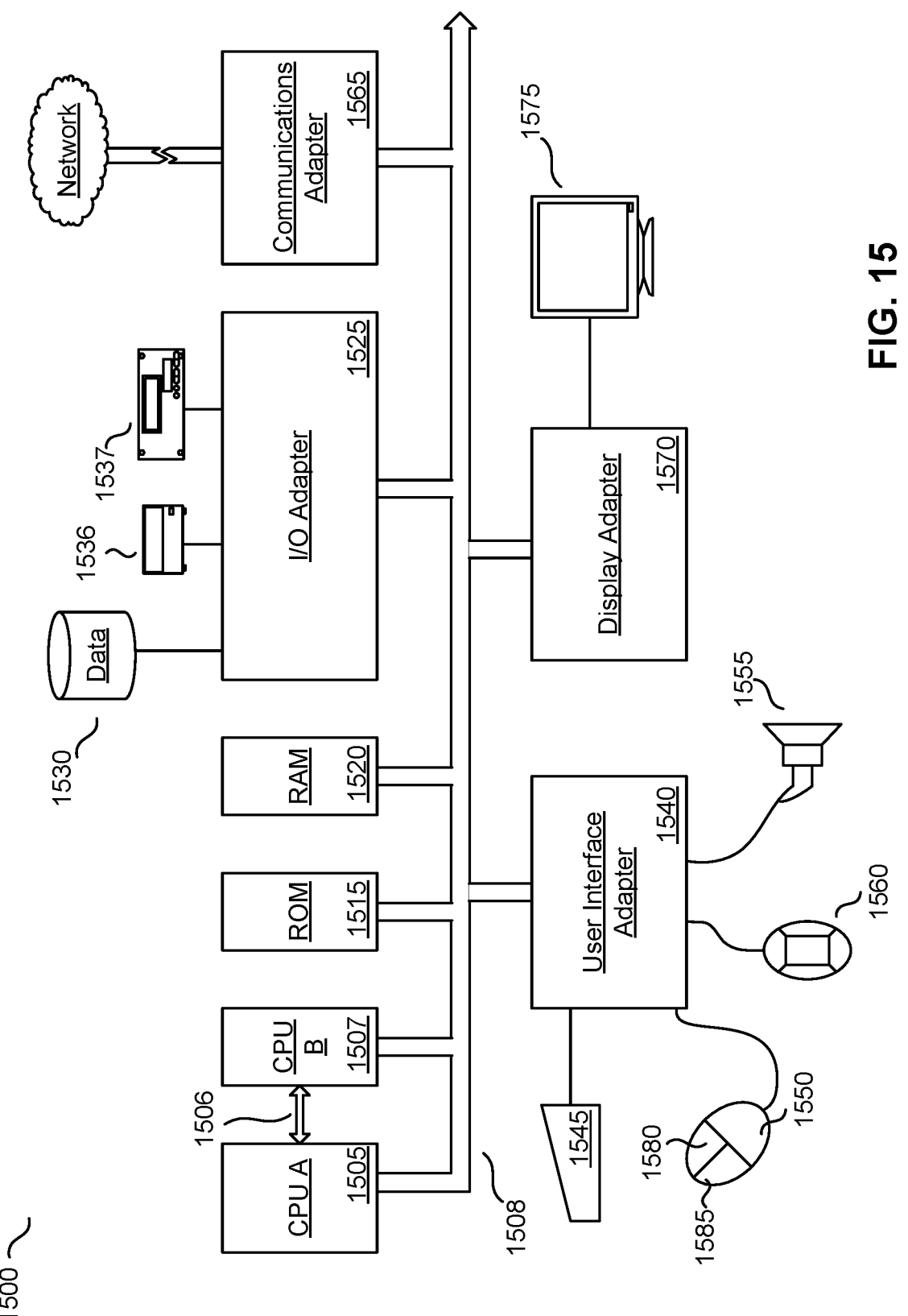
FIG. 15 is a high-level block diagram of a processing system in accordance with embodiments of the present disclosure.

Referring now to FIG. 15, a high-level block diagram of a processing system is illustrated and discussed. Methods and processes and other embodiments discussed previously may be implemented in a processing system executing a set of instructions stored in memory, or on a removable computer readable medium. An example of a processing system according to some embodiments is illustrated in FIG. 15. Computing system 1500 includes one or more central processing units, such as CPU A 1505 and CPU B 1507, which may be conventional microprocessors interconnected with various other units via at least one system bus 1508. CPU A 1505 and CPU B 1507 may be separate cores of an individual, multi-core processor, or individual processors connected via a specialized bus 1506. In some embodiments, CPU A 1505 or CPU B 1507 may be a specialized processor, such as a graphics processor, other co-processor, or the like.

Computing system 1500 includes random access memory (RAM) 1520; read-only memory (ROM) 1515, wherein the ROM 1515 could also be erasable programmable read-only memory (EPROM) or electrically erasable programmable read-only memory (EEPROM); and input/output (I/O) adapter 1525, for connecting peripheral devices such as disk units 1530, optical drive 1536, or tape drive 1537 to system bus 1508; a user interface adapter 1540 for connecting keyboard 1545, mouse 1550, speaker 1555, microphone 1560, or other user interface devices to system bus 1508; communications adapter 1565 for connecting processing system 1500 to an information network such as the Internet or any of various local area networks, wide area networks, telephone networks, or the like; and display adapter 1570 for connecting system bus 1508 to a display device such as monitor 1575. Mouse 1550 has a series of buttons 1580, 1585 and may be used to control a cursor shown on monitor 1575.

It is noted that terminologies as may be used herein such as bit stream, stream, signal sequence, etc. (or their equivalents) have been used interchangeably to describe digital information whose content corresponds to any of a number of desired types (e.g., data, video, speech, text, graphics, audio, etc. any of which may generally be referred to as 'data').

As may be used herein, the terms "substantially" and "approximately" provide an industry-accepted tolerance for its corresponding term and/or relativity between items. For some industries, an industry-accepted tolerance is less than one percent and, for other industries, the industry-accepted tolerance is 10 percent or more. Other examples of industry-accepted tolerance range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to".

As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information.

In embodiments where the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Furthermore, if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules, and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

As applicable, one or more functions associated with the methods and/or processes described herein can be implemented via a processing module that operates via the non-human "artificial" intelligence (AI) of a machine. Examples of such AI include machines that operate via anomaly detection techniques, decision trees, association rules, expert systems and other knowledge-based systems, computer vision models, artificial neural networks, convolutional neural networks, support vector machines (SVMs), Bayesian networks, genetic algorithms, feature learning, sparse dictionary learning, preference learning, deep learning and other machine learning techniques that are trained using training data via unsupervised, semi-supervised, supervised and/or reinforcement learning, and/or other AI. The human mind is not equipped to perform such AI techniques, not only due to the complexity of these techniques, but also due to the fact that artificial intelligence, by its very definition—requires "artificial" intelligence—i.e., machine/non-human intelligence.

As applicable, one or more functions associated with the methods and/or processes described herein can be implemented as a large-scale system that is operable to receive, transmit and/or process data on a large-scale. As used herein, a large-scale refers to a large number of data, such as one or more kilobytes, megabytes, gigabytes, terabytes or more of data that are received, transmitted and/or processed. Such receiving, transmitting and/or processing of data cannot practically be performed by the human mind on a large-scale within a reasonable period of time, such as within a second, a millisecond, microsecond, a real-time basis, or other high speed required by the machines that generate the data, receive the data, convey the data, store the data and/or use the data.

As applicable, one or more functions associated with the methods and/or processes described herein can require data to be manipulated in different ways within overlapping time spans. The human mind is not equipped to perform such different data manipulations independently, contemporaneously, in parallel, and/or on a coordinated basis within a reasonable period of time, such as within a second, a millisecond, microsecond, a real-time basis or other high speed required by the machines that generate the data, receive the data, convey the data, store the data and/or use the data.

As applicable, one or more functions associated with the methods and/or processes described herein can be implemented in a system that is operable to electronically receive digital data via a wired or wireless communication network and/or to electronically transmit digital data via a wired or wireless communication network. Such receiving and transmitting cannot practically be performed by the human mind because the human mind is not equipped to electronically transmit or receive digital data, let alone to transmit and receive digital data via a wired or wireless communication network.

As applicable, one or more functions associated with the methods and/or processes described herein can be implemented in a system that is operable to electronically store digital data in a memory device. Such storage cannot practically be performed by the human mind because the human mind is not equipped to electronically store digital data.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A system comprising:
one or more processors;
memory coupled to the one or more processors; and
instructions stored in the memory executed by the one or more processors, the instructions including instructions to:
    receive caregiver training data;
    provide the caregiver training data to a machine learning training module;
    store output of the machine learning module as a model, wherein the machine learning module output is based, at least in part, on the caregiver training data;
    receive caregiver input data associated with a particular caregiver;
    provide the caregiver input data to a machine learning evaluation module;
    provide the model to the machine learning evaluation module;
    receive caregiver evaluation output from the machine learning evaluation module, wherein the caregiver evaluation output is generated based, at least in part, on the model and the caregiver input data;
    store the caregiver evaluation output in a caregiver profile;
    select a caregiving solution based, at least in part, on the caregiver evaluation output; and
    provide, to a user, information associated with the caregiving solution.

2. The system of claim 1, wherein the machine learning training module comprises instructions to:
    perform first comparisons of individual information consumption preferences of individual caregivers to caregiver characteristics associated with the individual caregivers;
    establish first links between caregiver characteristics and information consumption preferences based on the first comparisons;
    perform second comparisons of sets of information consumption preferences of the individual caregivers to sets of caregiver characteristics associated with individual caregivers; and
    establish second links between sets of caregiver characteristics information and consumption preferences based on the first comparisons.

3. The system of claim 2, wherein the caregiver training data comprises individual information consumption preferences of individual caregivers and caregiver characteristics associated with the individual caregivers.

4. The system of claim 2, wherein the machine learning evaluation module comprises instructions to:
    receive the caregiver input data;
    evaluate the caregiver input data to identify information consumption preferences of the particular caregiver; and establish one or more links between the particular caregiver and one or more items of information conforming to the information consumption preferences of the particular caregiver.

5. The system of claim 4, wherein the caregiver input data comprises caregiver characteristics of the particular caregiver.

6. The system of claim 4, wherein the instructions further comprise instructions to update the first links and the second links based, at least in part, on the one or more links between the particular caregiver and the one or more items of information.

7. The system of claim 1 wherein the caregiver training data comprises information indicating consumption preferences associated with caregivers and caregiver characteristics of the caregivers.

8. The system of claim 1 wherein the model comprises a weighted links table comprising link values determined based on correspondences among the caregiver training data.

9. The system of claim 1 wherein the caregiver evaluation output comprises links to caregiver information preferences.

10. A method for operating a health-related application, the method comprising:
    receiving caregiver training data;
    providing the caregiver training data to a machine learning training module;
    storing output of the machine learning module as a model, wherein the machine learning module output is based, at least in part, on the caregiver training data;
    receiving caregiver input data associated with a particular caregiver;
    providing the caregiver input data to a machine learning evaluation module;
    providing the model to the machine learning evaluation module;
    receiving caregiver evaluation output from the machine learning evaluation module, wherein the caregiver evaluation output is generated based, at least in part, on the model and the caregiver input data;
    storing the caregiver evaluation output in a caregiver profile;
    selecting a caregiving solution based, at least in part, on the caregiver evaluation output; and
    providing, to a user, information associated with the caregiving solution.

11. The method of claim 10, further comprising:
    performing, by the machine learning training module, first comparisons of individual information consumption preferences of individual caregivers to caregiver characteristics associated with the individual caregivers;
    establishing, by the machine learning training module, first links between caregiver characteristics and information consumption preferences based on the first comparisons;
    performing, by the machine learning training module, second comparisons of sets of information consumption preferences of the individual caregivers to sets of caregiver characteristics associated with individual caregivers; and
    establishing, by the machine learning training module second links between sets of caregiver characteristics information and consumption preferences based on the first comparisons.

12. The method of claim 11, wherein the caregiver training data comprises individual information consumption preferences of individual caregivers and caregiver characteristics associated with the individual caregivers.

13. The method of claim 10, further comprising:

receiving, by the machine learning evaluation module, the caregiver input data;

evaluating, by the machine learning evaluation module, the caregiver input data to identify information consumption preferences of the particular caregiver; and establishing, by the machine learning evaluation module, one or more links between the particular caregiver and one or more items of information conforming to the information consumption preferences of the particular caregiver.

14. The method of claim 13, wherein the caregiver input data comprises caregiver characteristics of the particular caregiver.

15. The method of claim 13, further comprising updating the first links and the second links based, at least in part, on the one or more links between the particular caregiver and the one or more items of information.

16. One or more computer readable storage mediums having instructions stored thereon which, when executed by a processor, cause the processor to:

receive caregiver training data;

provide the caregiver training data to a machine learning training module;

store output of the machine learning module as a model, wherein the machine learning module output is based, at least in part, on the caregiver training data;

receive caregiver input data associated with a particular caregiver;

provide the caregiver input data to a machine learning evaluation module;

provide the model to the machine learning evaluation module;

receive caregiver evaluation output from the machine learning evaluation module, wherein the caregiver evaluation output is generated based, at least in part, on the model and the caregiver input data;

store the caregiver evaluation output in a caregiver profile;

select a caregiving solution based, at least in part, on the caregiver evaluation output; and provide, to a user, information associated with the caregiving solution.

17. The one or more computer readable storage mediums of claim 16, wherein the instructions further comprise instructions to:

perform, by the machine learning training module, first comparisons of individual information consumption preferences of individual caregivers to caregiver characteristics associated with the individual caregivers;

establish, by the machine learning training module, first links between caregiver characteristics and information consumption preferences based on the first comparisons;

perform, by the machine learning training module, second comparisons of sets of information consumption preferences of the individual caregivers to sets of caregiver characteristics associated with individual caregivers; and establish, by the machine learning training module, second links between sets of caregiver characteristics information and consumption preferences based on the first comparisons.

18. The one or more computer readable storage mediums of claim 16, wherein the instructions further comprise instructions to:

receive the caregiver input data;

evaluate the caregiver input data to identify information consumption preferences of the particular caregiver; and establish one or more links between the particular caregiver and one or more items of information conforming to the information consumption preferences of the particular caregiver.

19. The one or more computer readable storage mediums of claim 16, wherein the instructions further comprise instructions to update the first links and the second links based, at least in part, on the one or more links between the particular caregiver and the one or more items of information.

20. The one or more computer readable storage mediums of claim 16, wherein the model comprises a weighted links table comprising link values determined based on correspondences among the caregiver training data.

* * * * *